United States Patent
Gerhardt et al.

(10) Patent No.: US 7,186,336 B2
(45) Date of Patent: Mar. 6, 2007

(54) FLOW SENSING APPARATUS

(75) Inventors: Geoff C. Gerhardt, Millbury, MA (US); Joseph A. Luongo, Walpole, MA (US)

(73) Assignee: Waters Investments Limited, New Castle, DE (US)

( * ) Notice: Subject to any disclaimer, the term of this patent is extended or adjusted under 35 U.S.C. 154(b) by 187 days.

(21) Appl. No.: 10/851,497

(22) Filed: May 21, 2004

(65) Prior Publication Data

US 2005/0109698 A1    May 26, 2005

Related U.S. Application Data

(63) Continuation-in-part of application No. 10/723,973, filed on Nov. 26, 2003.

(51) Int. Cl.
*B01D 15/08* (2006.01)
(52) U.S. Cl. .................. 210/198.2; 210/101; 210/659; 422/70
(58) Field of Classification Search ................ 210/656, 210/659, 101, 198.2; 422/70
See application file for complete search history.

(56) References Cited

U.S. PATENT DOCUMENTS

| | | | |
|---|---|---|---|
| 3,917,531 A | 11/1975 | Magnussen | 210/31 |
| 4,003,243 A | 1/1977 | Blu | 73/61.1 |
| 4,174,772 A | 11/1979 | Neuss | 435/32 |
| 4,840,730 A | 6/1989 | Saxena | 210/198.2 |
| 5,004,538 A | 4/1991 | Apfel | 210/198.2 |
| 5,035,138 A | 7/1991 | Abdel-Rahman | 73/204.12 |
| 5,234,586 A | 8/1993 | Afeyan | 210/198.2 |
| 5,306,426 A | 4/1994 | Afeyan | 210/198.2 |
| 5,346,622 A | 9/1994 | Klee | 210/659 |
| 5,491,096 A | 2/1996 | Sportsman | 436/518 |
| 5,614,089 A | 3/1997 | Allington | 210/198.2 |
| 5,630,706 A | 5/1997 | Yang | 417/3 |
| 5,637,790 A | 6/1997 | de Corral | 73/54.06 |
| 5,938,932 A | 8/1999 | Connelly | 210/659 |
| 6,106,710 A | 8/2000 | Fischer | 210/659 |
| 6,386,050 B1 | 5/2002 | Yin | 73/861.95 |
| 6,402,946 B1 * | 6/2002 | Spraul et al. | 210/198.2 |
| 6,460,420 B1 | 10/2002 | Paul | 73/861.52 |

(Continued)

FOREIGN PATENT DOCUMENTS

DE    199 14 358 A1    10/2000

(Continued)

*Primary Examiner*—Ernest G. Therkorn
(74) *Attorney, Agent, or Firm*—Anthony J. Janiuk; Brian Michaelis

(57) ABSTRACT

A method and apparatus for monitoring and controlling the nano-scale flow rate of fluid in the operating flow path of a HPLC system. A first flow sensor is disposed in a first flow path between a first flow-divider and a fluidic tee. A second flow sensor is disposed in a second flow path between a second flow-divider and the fluidic tee. A first recycle flow restrictor is disposed in the first recycle flow path in fluid communication with the first flow-divider. A second recycle flow restrictor is disposed in the second The permeability of each recycle flow restrictor can be selected to produce a desired flow rate with each respective flow path. The output signals of the first and second flow sensors to control output of a pump within each flow path.

14 Claims, 11 Drawing Sheets

U.S. PATENT DOCUMENTS 6,627,075 B1 * 9/2003 Weissgerber et al. .... 210/198.2
6,712,085 B2 * 3/2004 Weissgerber et al. ......... 137/12
2002/0146349 A1 10/2002 Gygi ........................... 422/70
2002/0158022 A1 10/2002 Huang ........................ 210/656

FOREIGN PATENT DOCUMENTS

DE 199 14 358 C2 5/2001
EP 1 248 096 B1 10/2002
JP 4-115158 4/1992

* cited by examiner

FLOW SENSING APPARATUS

RELATED APPLICATIONS

The present application is a Continuation-In-Part of U.S. patent application Ser. No. 10/723,973 filed Nov. 26, 2003, entitled Flow Sensing Apparatus Used To Monitor/Provide Feedback To A Split Flow Pumping System, which is incorporated herein in its entirety.

FIELD OF THE INVENTION

The present invention relates to a flow sensing method and apparatus and more particularly to a flow sensing method and apparatus used to monitor and provide feedback to a split-flow pumping system which enables the delivery of stable flow to a nano-scale chromatographic system using a micro-scale or normal scale chromatographic pump.

BACKGROUND OF THE INVENTION

Traditional plunger displacement pumping systems have been successful in delivering stable, accurate flows in the normal-scale and micro-scale high performance liquid chromatography (HPLC) regimes. While normal-scale HPLC is performed with mobile phase flow rates of about 0.1–5.0 mL/min and micro-scale HPLC is performed with mobile phase flow rates of about 1–100 µL/min, nano-scale HPLC requires mobile phase flow rates in the 50–500 nL/min range. Plunger displacement pumping systems can not deliver nano-scale HPLC flow rates with reliability and accuracy.

One method for providing nano-scale flow rates in an HPLC system is to use a flow-divider which directs a majority of flow from the pump to a waste stream and a small portion of the pump output to the HPLC working stream (i.e., to the liquid chromatography column). A split restrictor in the waste stream and/or the working stream controls the split ratio of the system. Normal-scale or micro-scale HPLC pumps can be used in split flow mode to produce nano-scale HPLC flow rates in the working stream.

In order to operate an HPLC system in split-flow mode the user must calculate the split ratio of the system. To calculate the split ratio, the user must know the permeabilities of both the split restrictor and the chromatographic system (i.e. the packed column). These permeabilities are used to calculate the flow rate that must be supplied by the normal-scale or micro-scale HPLC pump to produce the desired flow through the chromatographic system. Although it is possible to calculate split restrictor dimensions that should provide a desired split ratio, changes in permeability of either the split restrictor or chromatographic column over time cause unpredictable split ratio variations. Such variations result in unacceptable flow variations through the chromatographic column.

One possible solution to the problem of changing split ratios is to monitor the flow to the chromatographic column with an appropriate flow sensor. Fluid flow rates can be determined by measuring the pressure of a liquid flowing through a restrictor. Assuming a constant viscosity, the back pressure of liquid flowing through a restrictor will scale linearly with the flow rate of the liquid. The flow rate is measured by placing a pressure transducer before and after a restrictor inline with the flow. Signals from the pressure transducers are electronically subtracted and amplified to achieve a high degree of common-mode noise rejection.

The permeability of the restrictor is chosen so that it provides sufficient back pressure to produce a measurable pressure difference signal (ΔP) in the flow ranges of interest but does not produce a significant back pressure for the pump. For example, a 10 cm long, 25 µm inside diameter capillary will provide a back pressure of approximately 100 pounds per square inch (psi) for water flowing at 5 µL/min. This permeability is sufficient for providing a flow measurement while not inducing much fluidic load on the pump.

However, pressure measuring flow sensors must be calibrated to compensate for the different viscosity of each fluid being measured. This creates a great disadvantage in liquid chromatography applications wherein fluid composition varies dramatically over the course of a chromatography run.

Another method that can be used to sense fluid flow is thermal flow sensing. Several companies including Sensirion AG, of Zurich, Switzerland, and Bronkhorst Nijverheidsstraat of Ruurlo, The Netherlands, have been developing thermal flow sensors capable of monitoring flows in nL/min ranges.

Operation of these thermal flow sensors is described with reference to FIG. 1. Heat introduced into a liquid filled tube/channel will disperse in both the upstream and downstream directions (i.e. due to thermal conduction or diffusion respectively). The tube of the flow sensing device is made from materials of low thermal conductivity (i.e. glass, plastic). A temperature profile similar to curve "A" in FIG. 1 will develop when a discrete section of the fluid in the tube is continuously heated, under a zero flow condition. The shape of this temperature profile will depend upon the amount of heat added to the fluid and the upstream and downstream temperatures of the liquid. Assuming identical upstream and downstream fluid temperatures, under a zero-flow condition, liquid temperatures measured at $P_1$ and $P_2$ will be equal as thermal diffusion will be equal in both directions.

If the liquid in the tube is permitted to flow, the fluid temperatures at $P_1$ and $P_2$ will depend upon the rate of liquid flux and the resulting heat convection. As liquid begins to flow past the heated zone, a temperature profile similar to curve B in FIG. 1 will develop. In addition to the symmetric diffusion of the heat, asymmetric convection of the heated fluid will occur in the direction of the fluid flow. Therefore, under flowing conditions, fluid temperatures measured at $P_1$ and $P_2$ will be different.

Temperature measurements made at $P_1$ and $P_2$ are sampled, subtracted and amplified electronically in situ to provide a high degree of common-mode noise rejection. This allows discrimination of extremely small upstream and downstream temperature differences. By appropriate placement of temperature measurement probes (i.e., $P_1$ and $P_2$) and/or by changing the amount of heat added to the flowing liquid, temperature measurement can be made at inflection points along the temperature profile. Measurement at the inflection points maximizes the upstream/downstream ΔT response to flow rate change.

The dynamic range of thermal flow sensing is limited by the sensitivity and precision of the temperature measurement instruments. Heat transfer via diffusion in the fluid and heat transfer to the tube walls occurs rapidly under low fluid flux conditions (i.e. <500 nL/min in tubing/channels of dimensions <100 um). Therefore, precise measurement of temperature close to the point of heat addition is required. The upper dynamic range is limited by the dynamic range of the temperature sensors and by the amount of heat that can be added to the flowing liquid.

However, like pressure measuring flow sensors which must be calibrated to compensate for the different viscosity of each fluid being measured. Thermal based flow sensors also need such calibration. This creates a great disadvantage in liquid chromatography applications wherein fluid composition varies dramatically over the course of a chromatography run.

SUMMARY OF THE INVENTION

The present invention provides a method and apparatus for monitoring and controlling the nano-scale flow rate of fluid in the operating flow path of a HPLC system without relying on complex calibration routines to compensate for solvent composition gradients typically used in HPLC. A main flow sensor is disposed in the main flow path between the pump and a flow-divider. A second flow sensor is disposed in either the waste flow path downstream of the splitter or in the operating flow path. When the second flow sensor is disposed in the waste flow path, the output signal of the second flow sensor is subtracted from the output signal of the main flow sensor in a difference circuit to obtain an indirect measure of the flow through the operating flow path. When the second flow sensor is disposed in the operating flow path, the flow through the operating flow path is measure directly. In either case, the flow measured by the main flow sensor (i.e. the input flow to the system) is divided by the flow measured through the operating flow path (i.e. that measured indirectly by measurement of the flow through the waste flow path or that measured directly by a flow sensor in the operating flow path) in a divider circuit. The output of the divider circuit represents an empirical split ratio of the flow-divider and is independent of media composition and system permeability. The divider circuit output can optionally be fed back to a control circuit to adjust the waste stream flow rate to a desired value, for example by controlling a variable restrictor in the waste flow path or adjusting the pump flow rate to obtain a desired flow in the operating flow path. The controlled flow rates are thereby based on a measured flow ratio.

Thermal flow sensors or pressure measuring sensors as described hereinbefore can be used as upstream, waste or operating stream flow sensors with good accuracy and precision. When the flow sensor is used in the operating path, in order to obtain acceptable accuracy and precision, a sensor of different scaling from the main flow sensor is used (i.e. for a pressure-based flow sensor, a less permeable restrictor is used to produce a measurable pressure drop for nano-scale flow rates, for a thermal-based flow sensor, the sensing elements' thermal mass is scaled to allow measurement of nano-scale mass flow rates).

An illustrative embodiment of the invention includes an apparatus for measuring flow rates of a liquid in a capillary system. A main flow path carries liquid to a flow-divider. An operating flow path carries a portion of the liquid from the flow-divider according to a split ratio of the flow-divider. A waste flow path carries the remaining portion of the liquid from the flow-divider. A main flow sensor is operatively disposed with the main flow path and configured to measure volumetric flow rates of the liquid in the main flow path. A waste flow sensor is operatively disposed in the waste flow path and configured to measure volumetric flow rates of the liquid in the waste flow path. A subtractor receives a main flow signal from the main flow sensor and a waste flow signal from the waste flow sensor. The subtractor is configured to provide a difference signal representing the difference between the main flow signal and the waste flow signal. A divider receives the difference signal and the main flow signal. The divider is configured to provide a quotient signal representing the split ratio of the flow-divider.

In an illustrative embodiment, the capillary system is a high pressure liquid chromatography (HPLC) system having operating stream flow rates in the nano-scale range. The subtractor is typically implemented as an electronic subtraction circuit and the divider is typically implemented as an electronic divider circuit. The quotient signal is independent of solvent composition.

In another illustrative embodiment the main flow sensor and the waste flow sensors are thermal-type flow sensors. The thermal-type flow sensors include means for introducing heat in a flow path and means for measuring temperature (i.e., temperature sensors) of liquid in the flow path upstream and downstream of the point of introducing the heat. The thermal-type flow sensors also include means, such as a thermal flow calculator described hereinafter, for computing the volumetric flow rate of liquid in the flow path according to differences between upstream and downstream temperatures in the flow path.

In another illustrative embodiment, the main flow sensor and the waste flow sensor are pressure-type flow sensors. The pressure-type flow sensors include restrictor means disposed in a flow path and means for measuring fluid pressure upstream and downstream of the restrictor means. The pressure-type flow sensors also include means for computing the volumetric flow rate of liquid in the flow path according to the difference between pressure measured upstream of the restrictor and pressure measured downstream of the restrictor means. The means for computing volumetric flow rate of liquid can include, for example, subtractor means implemented to provide the difference (i.e., pressure drop) in pressure measured upstream and downstream of a restrictor means. Alternatively, virtually any electronic computation means can be implemented to determine liquid flow rate as a function of pressure drop across a restrictor means.

Another illustrative embodiment of the invention includes a controller that receives the quotient signal from the divider. The controller is configured to adjust the liquid flow rate in the operating flow path in response to the quotient signal. In at least one embodiment, the system includes a waste path variable restrictor operatively disposed in the waste flow path. The waste path variable restrictor is responsive to a signal from the controller to adjust the liquid flow rate in the operating flow path by varying permeability of the waste flow path. Another embodiment of the invention includes a main path pump operatively disposed in the main flow path. The main path pump 26 is responsive to a signal from the controller to adjust the liquid flow rate in the operating flow path 14 by varying output flow of the main pump.

In another illustrative embodiment, the present invention includes a method for measuring nano-scale flow rates of a liquid in a high pressure liquid chromatography (HPLC) system. The method includes measuring a main flow rate in a main flow path between a HPLC pump and a flow-divider. The flow-divider divides the main flow path into an operating flow path and a waste flow path according to a split ratio of the flow-divider. The method further includes measuring a waste flow rate in the waste flow path, subtracting the waste flow rate from the main flow rate to determine a flow rate difference and dividing the flow rate difference by the main flow rate to determine an empirical split ratio. The empirical split ratio is independent of varying liquid composition.

According to the invention, the liquid flow rate in the operating flow path can be adjusted in response to the empirical split ratio. In at least one embodiment, the liquid flow rate in the operating flow path is adjusted by changing the permeability of a variable restrictor disposed in the waste flow path. In another embodiment, the liquid flow in the operating flow path is adjusted by changing the output flow rate of the HPLC pump.

In yet another illustrative embodiment, the present invention includes a method and apparatus for measuring nano-scale flow rates of a liquid in a binary solvent delivery high pressure liquid chromatography (HPLC) system. The method and apparatus include selecting a recycle flow restrictor in each flow path, of the binary solvent delivery system, having a permeability allowing for diversion of fluid from the flow path in excess of desired delivery rates.

In a further illustrative embodiment, the present invention includes a method and apparatus for measuring nano-scale flow rates of a liquid in a binary solvent delivery high pressure liquid chromatography (HPLC) system. The method and apparatus include the use of a first pressure transducer in a first pressure flow path and a second pressure transducer in a second pressure flow path where each pressure flow path is in fluid communication with a fluidic cross. The fluidic cross is in fluid communication with a fluidic cross pressure transducer. A pressure drop measurement between the first pressure transducer and the fluidic cross pressure transducer and the second pressure transducer and the fluidic cross pressure transducer will be proportional to the flow delivered by a first pump within the first pressure flow path and a second pump in the second pressure flow path respectively.

Illustrative embodiments of the present invention feature a method for measuring and controlling nano-scale flow rates in a capillary system by measuring liquid flow in the high flow rate range. In applications wherein nanoscale flow sensors are not available or are prohibitively expensive, for example, sensors that are precise, accurate and readily available are configured in the high volume stream and used to monitor and control the related nano-scale flow rate in the operating stream. A method for accurately measuring and controlling capillary fluid flows in the nL/min (nano-scale) range is provided that is not sensitive to changes in the fluid composition over time. Accordingly, the present invention is particularly useful to measure and control the operating stream to an LC (liquid chromatography) column in a HPLC system.

The present invention effectively avoids the need to calibrate thermal type sensors according to the thermal conductivity of each liquid being measured. Pressure-type thermal flow sensors may also be used within the accurate operating range of the pressure-type sensors. The present invention substantially eliminates the need to calibrate the pressure type sensors according to the viscosity of each liquid being measured or the changing permeability of the capillary system. Advantageously, the invention also minimizes the delay caused by the large internal volume of pressure-type flow sensors, by positioning the sensors in an appropriate location, such as outside of the nano-scale flow path. In applications where suitable nano scale flow sensors are not available, embodiments of the present invention provide a method and apparatus for sensing nano scale flow rates with thermal flow sensors within the accurate operating range of the thermal flow sensors.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 3:
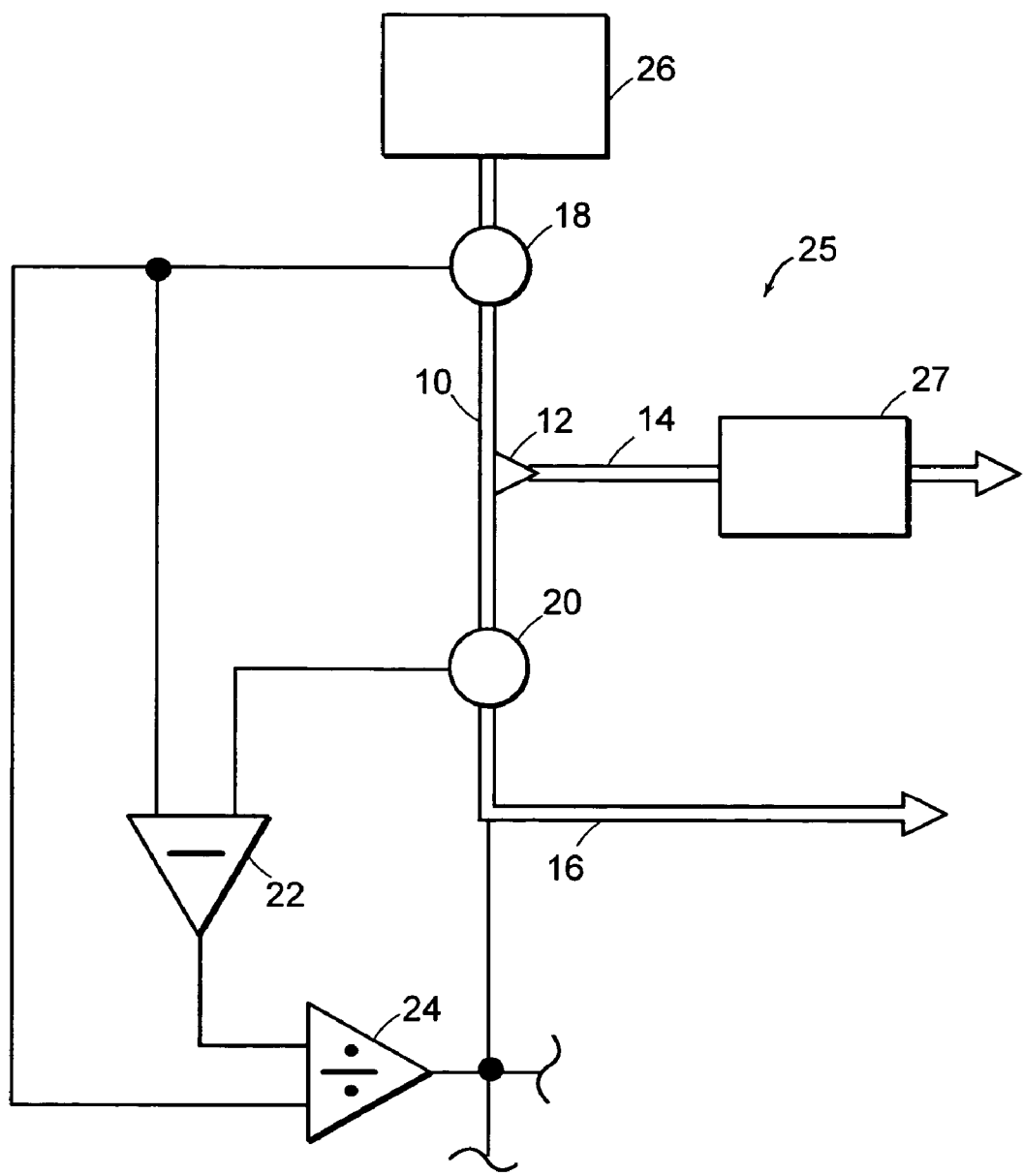
FIG. 3 is a schematic system diagram of an apparatus for measuring nano-scale flow rates of liquid in a capillary system according to an illustrative embodiment of the present invention.

An illustrative embodiment of a capillary system 25 according to the invention is described generally with reference to FIG. 3. A main flow path 10 is divided by a flow-divider 12 into an operating flow path 14 and a waste flow path 16. A main flow sensor 18 is operatively disposed in the main flow path 10. A waste flow sensor 20 is operatively disposed in the waste flow path 16. Outputs from both the main flow sensor 18 and the waste flow sensor 20 are connected to the input of a subtractor 22 for communicating volumetric flow rate signals to the subtractor 22. Outputs from both the main flow sensor 18 and the subtractor 22 are connected to inputs of a divider 24 for communicating the main volumetric flow rate signal and a difference signal to the divider 24. The output of the divider 24 can be used, for example as described hereinafter to control flow rate in an operating stream.

Figure 4:
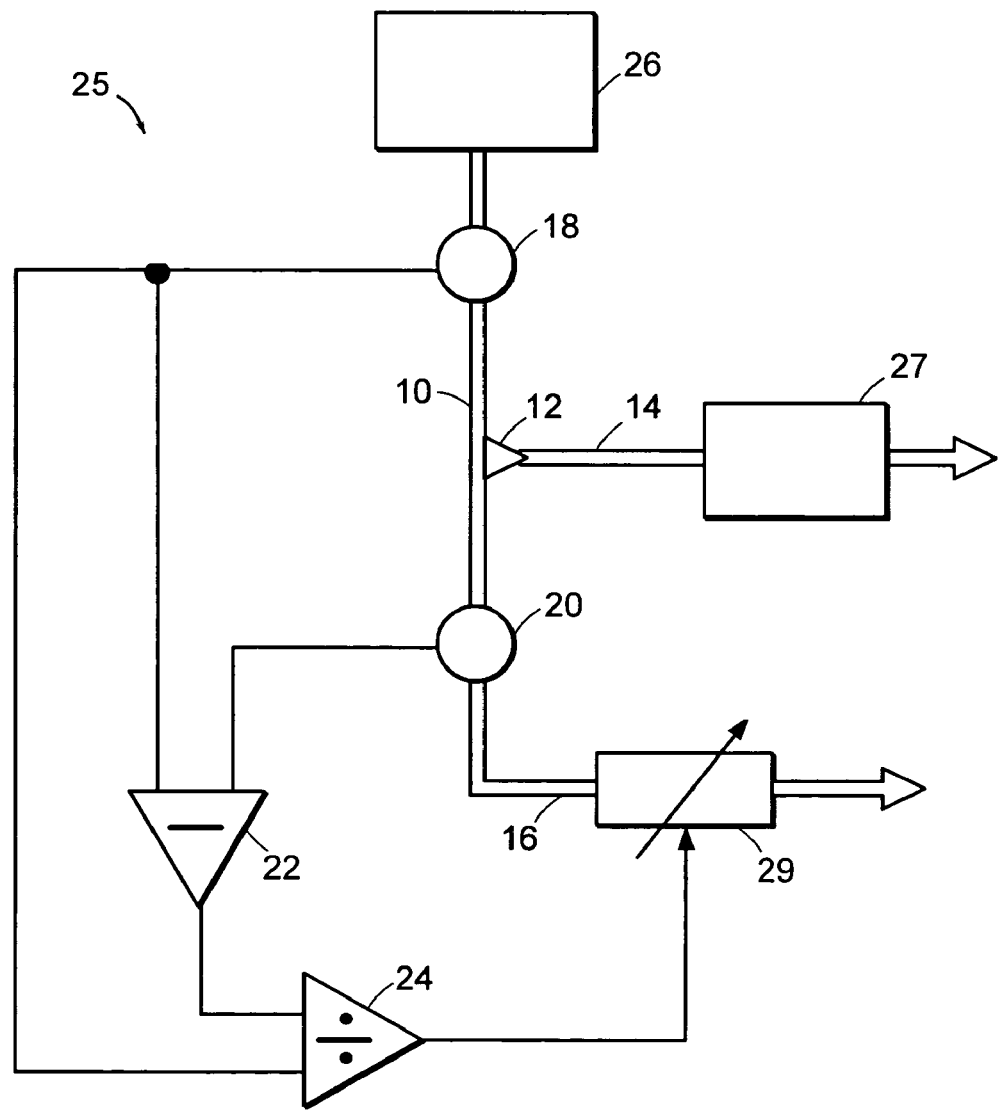
FIG. 4 is a schematic system diagram of an apparatus for measuring and controlling nano-scale flow rates in a capillary system using a variable restrictor in the waste flow path according to an illustrative embodiment of the present invention.

In an illustrative embodiment depicted in FIG. 4, the capillary system 25 is a high pressure liquid chromatography (HPLC) system. In the HPLC system, a pump 26 is operatively disposed in the main flow path 10. An HPLC column 27 is disposed in the operating flow path 14. The pump 26 is configured to provide an appropriate flow rate to the liquid (mobile phase) in the main flow path 10. The flow divider 12 and a split restrictor 29 are configured to deliver an appropriate portion of the mobile phase to the operating stream.

In an HPLC system, a normal scale HPLC pump 26 can be employed to provide a flow rate in the range of about 0.1 to 5.0 mL/min of mobile phase in the main flow path 10. A micro scale HPLC pump 26 can alternatively be employed to provide a flow rate in the range of about 1 to 100 μL/min. in the main flow path 10. The flow-divider 12 and split restrictor 29 are designed or selected to provide a split ratio appropriate to provide mobile phase to the operating flow path 14 at the desired nano-scale (nL/min.) flow rate. In alternative embodiments of the present invention the flow-divider 12 can be designed or selected to have a split ratio to provide mobile phase to the operating flow path at a desired capillary scale (1–20 μL/min) or micro-bore scale (20–100 μL/min) flow rate, for example. The flow-divider 12 includes at least one fluid restrictor (not shown) in the waste flow path 16 and/or the operating flow path 14 to achieve a desired split ratio. The resulting flow rate of mobile phase flow in the waste flow path 16 is therefore in approximately the same range as the flow rates in the main flow path 10. That is, both the main flow path 10 and waste flow path 16 carry large flow volumes compared to the nano-scale flow volumes carried by the operating flow path 14.

Any of various flow sensors capable of providing precise and accurate output signals in the micro-scale flow range can be used to implement the main flow sensor 18 and waste flow sensor 20 according to the illustrative embodiment of the invention. It is envisioned that flow sensors that provide precise and accurate output signals in the normal-scale flow range would be suitable for use as the main flow sensor 18 and/or as the waste flow sensor 20 in systems having a pump 26 configured to provide normal-scale flow in the main flow path 10. In at least one embodiment, the waste flow sensor is disposed between the flow divider 12 and split restrictor 29. This allows sensing before any delay caused by flow through the split restrictor during which solvent composition could be changing, for example.

Figure 5:
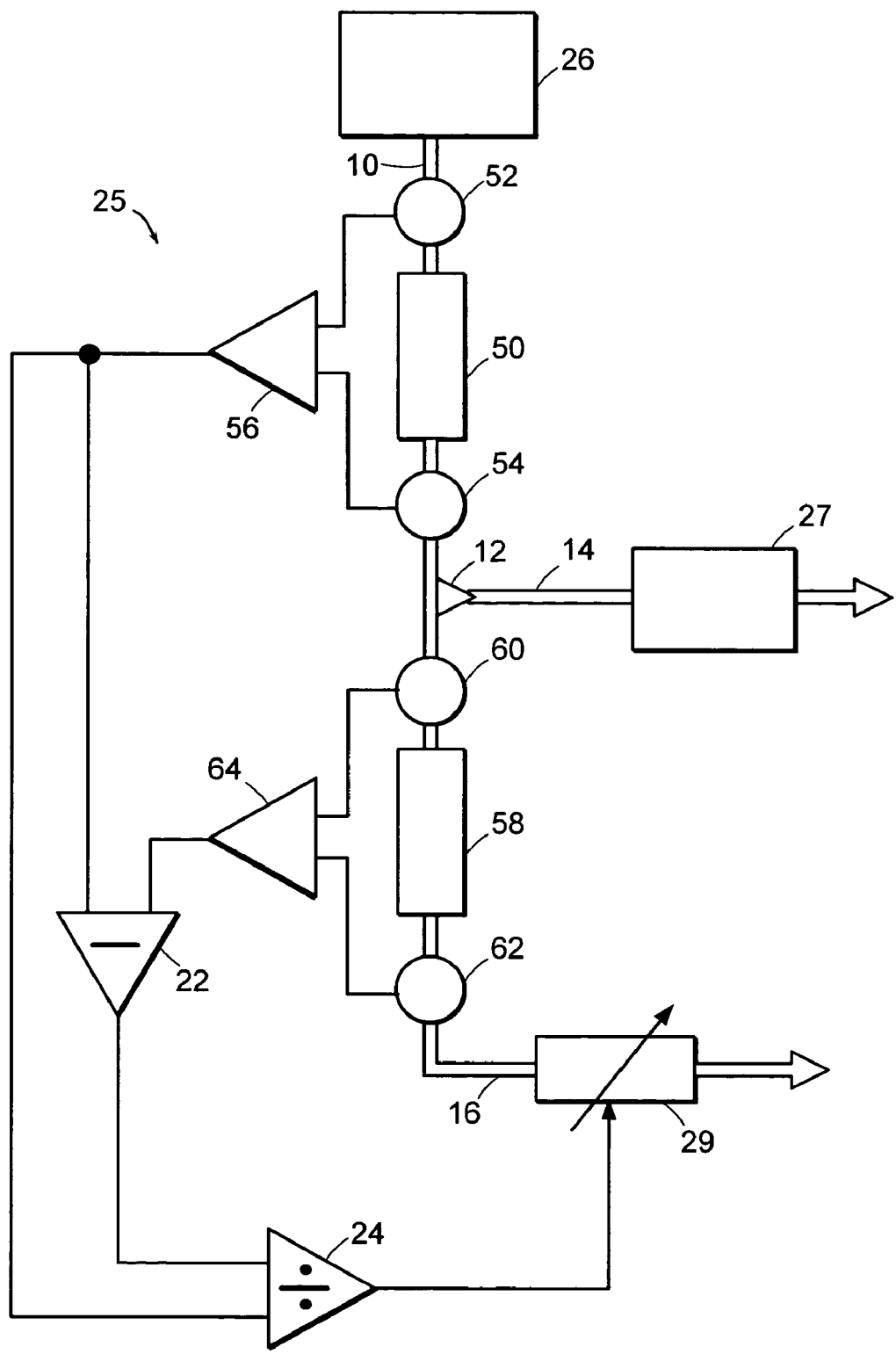
FIGS. 5 and 6 are schematic system diagrams of an apparatus for measuring and controlling nano-scale flow rates in a capillary system using pressure-type flow sensors in the main flow path and in the waste flow path according to illustrative embodiments of the present invention.
Figure 6:
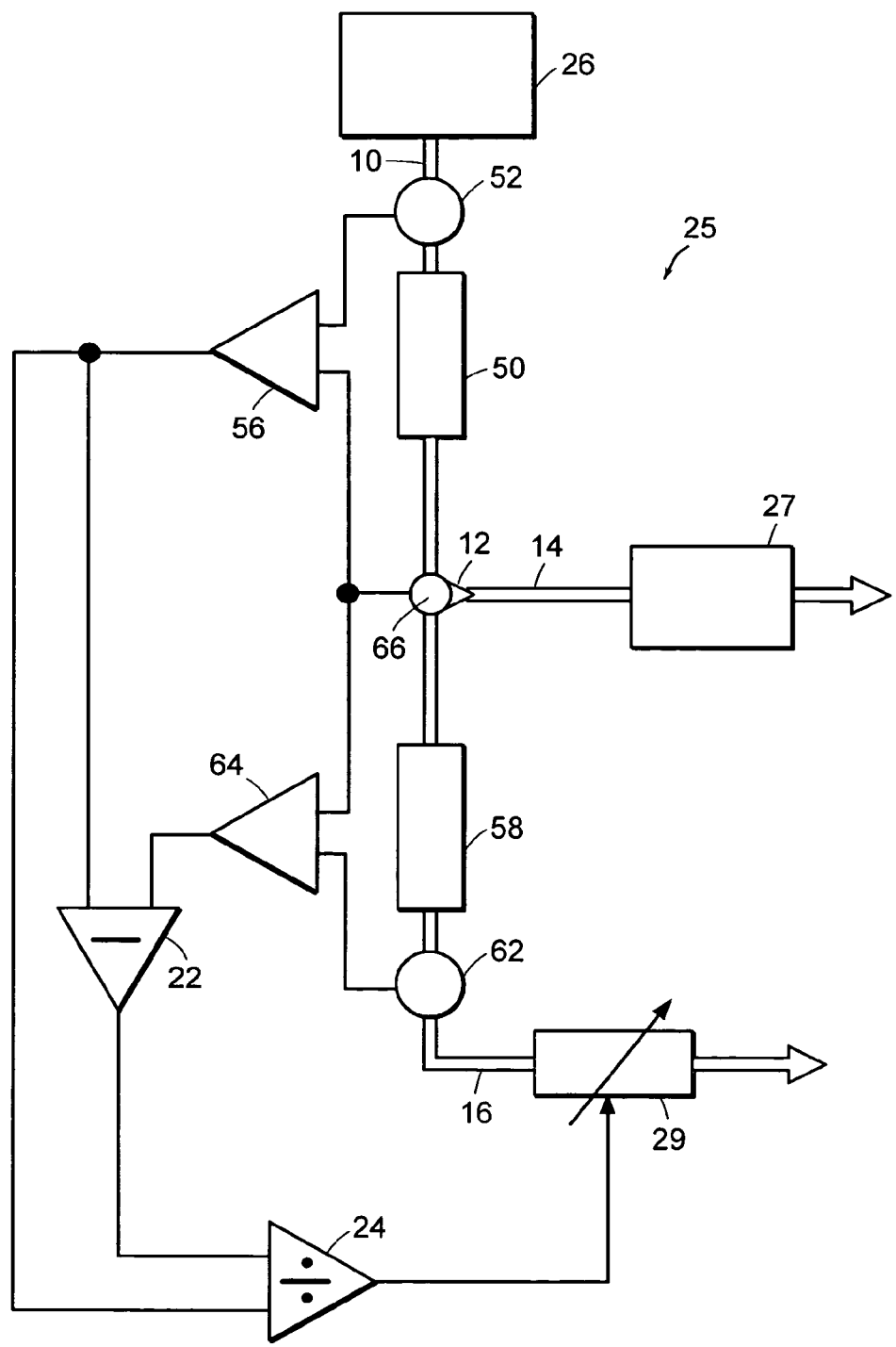
Figure 7:
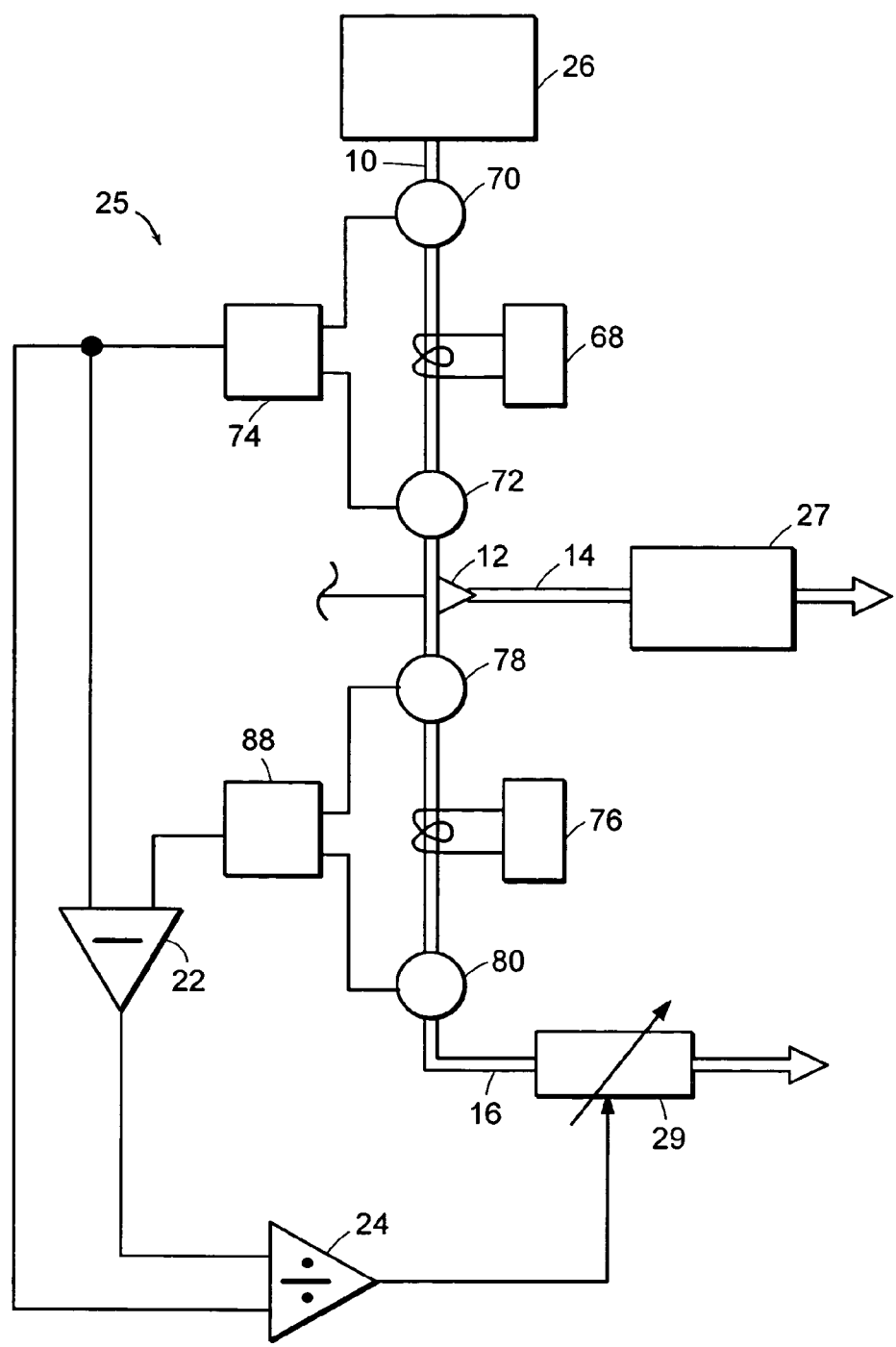
FIG. 7 is a schematic system diagram of an apparatus for measuring and controlling nano-scale flow rates in a capillary system using temperature-type flow sensors in the main flow path and in the waste flow path according to an illustrative embodiment of the present invention.

Various illustrative embodiments of flow sensors suitable for use as the main flow sensor 18 and/or the waste flow sensor 20 according to the present invention are described infra with respect to FIGS. 5–7. The measurement drift that is typically encountered at nano-scale HPLC flow rates is minimized because the flow measurements provided by the main flow sensor 18 and waste flow sensor 20 are made at relatively high mass flow rates.

The subtractor 22 is implemented as an electronic subtraction circuit as known to those skilled in the art. Input signals to the subtractor 22 represent the flow rate of mobile phase in the main flow path 10 and the flow rate of mobile phase in the waste flow path 16. The difference between these two flow rates represents the mobile phase flow rate in the operating flow path 14 and is represented in the output signal of the subtractor 22.

The divider 24 is implemented as an electronic divider 24 circuit as known to those skilled in the art. Input signals to the divider 24 represent the flow rate of the mobile phase in the main flow path 10 and the flow rate of the mobile phase in the operating flow path 14. Accordingly, the divider 24 outputs a signal representing the split ratio of the flow-divider 12. The signal output by the divider 24 according to the present invention is independent of the composition of the liquid being measured (mobile phase). Accordingly, in contrast to heretofore known systems for measuring flow rates in a range from about 10 nL/min. to about 1000 mL/min. which must typically be calibrated for particular liquid composition, the flow sensing method of the present invention is insensitive to the composition of the fluid being measured.

In an illustrative embodiment of the invention, output from the divider 24 is used to control the flow rate in the operating stream. FIG. 4 illustrates an embodiment of the invention wherein the flow rate in the operating stream is controlled by adjusting a the permeability of a waste path variable resistor, in the form of a variable restrictor 29 disposed in the waste flow path 16 and operatively connected to the output of the divider 24. Persons having ordinary skill in the art should appreciate that additional control circuitry (not shown) may be required between the output of the divider 24 and the input of the variable restrictor. For example, additional control circuitry may be implemented to condition the divider 24 output signal for use as an appropriate control input to the particular variable restrictor being used. Circuit components such as buffers, inverters, amplifiers and/or microcontrollers, for example, can be used to implement the control circuitry according to a number of methods that are well known to those skilled in the art.

In illustrative embodiments of the invention, a microcontroller or microprocessor (not shown) is implemented between the divider 24 output and the control input of the variable restrictor. The microcontroller or microprocessor can be programmed and configured, for example, to adjust the permeability of the variable restrictor and/or the flow rate of the pump 26 to a setting appropriate for maintaining a constant flow rate in the operating flow path 14.

An illustrative embodiment of a capillary system 25 according to the present invention using pressure-type flow sensors is diagrammed in FIG. 5. A restrictor means 50, 58 is disposed in both the main flow path 10 and the waste flow path 16. Restrictor means can include virtually any structure or method for impeding the flow of fluid in a flow path in a predictable manner to create a predictable pressure drop from one side of the restrictor means to the other. For example, a length of capillary tubing having a precisely dimensioned inside diameter can be a suitable restrictor means in some embodiments of the invention. It is envisioned that screens, filters and other impediments to flow could also be disposed in the flow path for use as restrictor means in various embodiments of the invention. Certain other embodiments of the invention require variable restrictor means wherein the impediment to fluid flow can be controlled as known in the art.

Pressure sensing means 52, 54, 60, 62 are operatively disposed upstream and downstream of each restrictor means 50, 58 in their respective flow path. Pressure sensing means suitable for the use in the present invention can include pressure transducers that are commonly available. Pressure sensing means should have an operating range and precision suitable to accurately detect the pressure drop across a particular restrictor. Pressure sensing means 52, 54, 60, 62 may include virtually any type of pressure sensor providing an electronic output signal and having sufficient accuracy and precision to measure pressure within the dynamic range of the fluid system.

Typical pressure sensing means generate analog voltage signals having a magnitude proportional to the pressure being sensed. It is envisioned that virtually any type of output from an appropriate pressure sensing means could be used in the present invention. For example, it is envisioned that various pressure sensing means could generate a pressure dependent electric current, a pressure dependent modulated signal, a pressure dependent variable resistance, a variable capacitance, an optical signal and the like. Accordingly, certain pressure sensing means also incorporate various other components, for example, as signal conditioning components, to amplify an output signal or convert the signal to a form more suitable for use in a particular system.

The outputs of the upstream and downstream pressure sensing means 52, 54 in the main flow path 10 are connected to main flow path 10 pressure subtractor means 56. Subtractor means include virtually any electronic subtraction circuitry as known in the art. Suitable subtractor means can include, for example, a standard operational amplifier (op-amp) subtraction circuit. Alternatively, an analog to digital (A/D) converter can be implemented to convert a signal to digital form so digital subtractor means such as a microcontroller, or personal computer can be used as subtractor means as known in the art. The outputs of the upstream and downstream pressure sensing means 60, 62 in the waste flow path 16 are connected to waste flow path 16 pressure subtractor means 64. Outputs from the main stream pressure subtractor means 56 and waste stream pressure subtractor means 64 correspond to output of the main flow sensor 18 and waste flow sensor 20, respectively (see FIGS. 3 and 4), and are connected to the input of the subtractor 22. The inputs to the subtractor 22 correspond to the flow rates in the main flow path 10 and the waste flow path 16 because the flow through each restrictor is linearly related to the pressure drop across it.

Another embodiment of a capillary system 25 according to the present invention using pressure-type flow sensors is diagrammed in FIG. 6. A restrictor means 52, 58 is disposed in both the main flow path 10 and the waste flow path 16. Pressure sensing means are operatively disposed upstream and downstream of each restrictor means in their respective flow path. However, in the embodiment depicted in FIG. 6, a single flow-divider pressure sensing means 66 serves to measure fluid pressure down stream of restrictor 50 in the main flow path 10 and upstream of the restrictor 58 in the waste flow path 16. The system illustrated in FIG. 6 is substantially similar to the system illustrated in FIG. 5 except that a single pressure sensing means is used to provide a measurement of liquid pressure on the downstream side of the main stream restrictor and on the upstream side of the waste stream restrictor. The single pressure sensing means is incorporated with the flow-divider 12.

The outputs of the upstream pressure sensing means 52 and flow-divider pressure sensing means 66 in the main flow path 10 are connected to main flow path 10 pressure subtractor means 56. The outputs of the flow-divider pressure sensing means 66 and downstream pressure sensing means 62 in the waste flow path 16 are connected to waste flow path pressure subtractor means 64. Outputs from the main stream pressure subtractor 22 means and waste stream pressure subtractor 22 means correspond to output of the main flow sensor 18 and waste flow sensor 20, respectively (see FIGS. 3 and 4), and are connected to the input of the subtractor 22. The inputs to the subtractor 22 correspond to the flow rates in the main flow path 10 and the waste flow path 16 because the flow through each restrictor is linearly related to the pressure drop across it.

Figure 1:
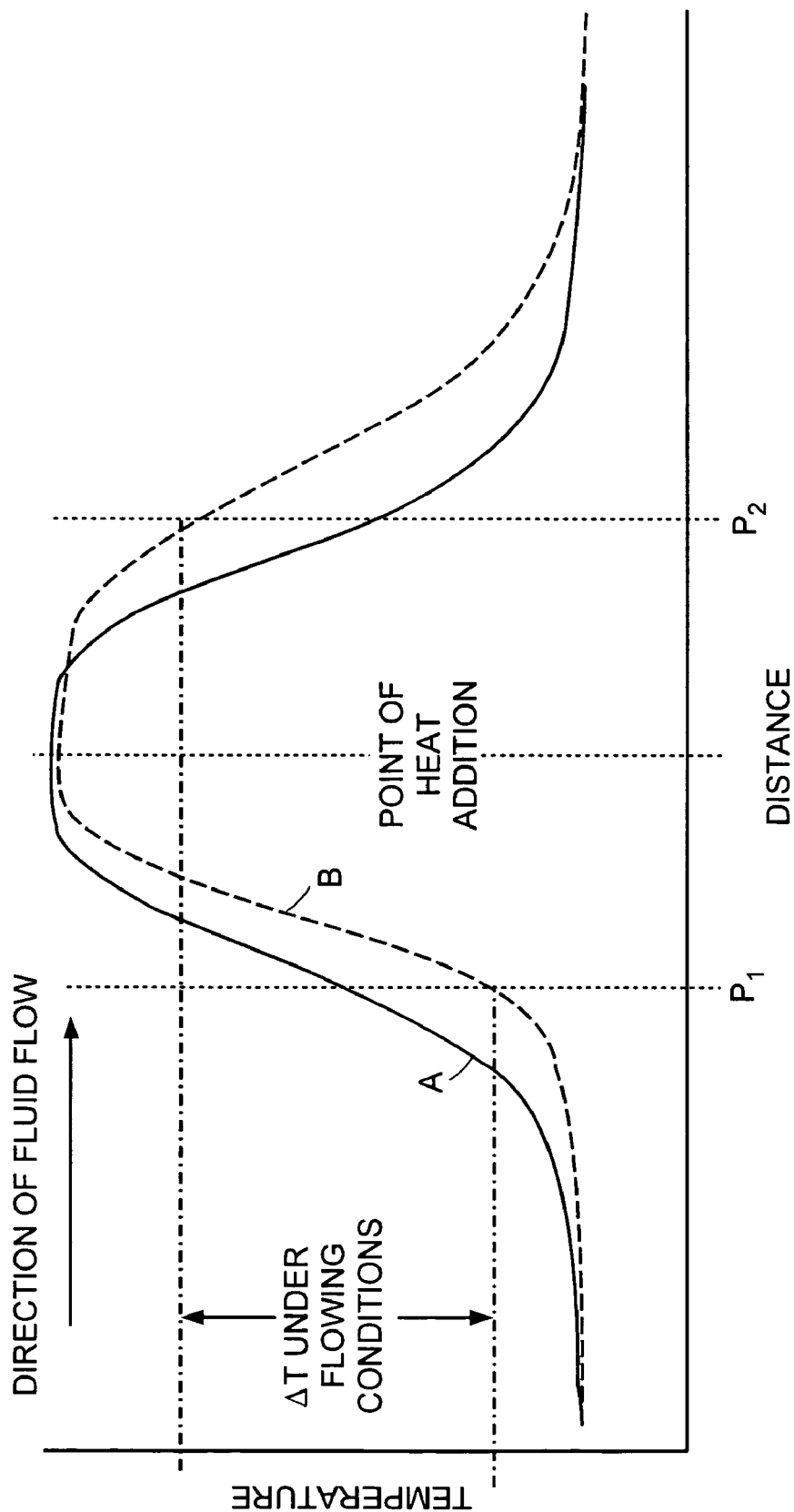
FIG. 1 is a graphical representation of the temperature distance between sensors used in thermal—type flow sensing according to the PRIOR ART.

FIG. 7 illustrates an embodiment of the invention which uses thermal-type flow sensors. In the illustrative embodiment depicted in FIG. 7, a means for introducing heat, i.e., a main path heater 68 is disposed at a discrete location to inject heat into the fluid flowing in the main flow path. The means for introducing heat can include any structure or method for heating a discrete segment of the fluid stream. For example, it is envisioned that an electric heater coil connected to an accurate temperature controller can be wrapped around a small segment of the flow path. Main path temperature sensors 70, 72 are placed upstream and downstream of the main path heater 68. Outputs from the main path temperature sensors 70, 72 are communicated to a main path thermal flow calculator 74. A waste path heater 76 is disposed at a discrete location to inject heat, i.e., a heat plug, into the fluid flowing in the waste flow path 16. Waste path temperature sensors 78, 80 are placed upstream and downstream of the waste path heater 76. Outputs from the waste path temperature sensors 78, 80 are communicated to a waste path thermal flow calculator 88. The main path thermal flow calculator 74 and waste path thermal flow calculator 88 are components of the thermal flow sensors described hereinbefore with respect to FIG. 1 which each compute the flow rates in their corresponding flow paths according to means well known in the art. Each thermal flow calculator 74, 88 outputs a signal representing the flow rate in its corresponding flow path.

A number of electronic circuits known in the art can serve as thermal flow calculators 74, 88 according to the present embodiment. For example, microprocessor circuits, microcontrollers, ASICs (application specific integrated circuits), or analog comparison circuitry are all well known in the art and can be configured to compare outputs from the temperature sensors 70, 72, 78 and 80 and calculate fluid flow rates in their respective flow path. Alternatively, thermal flow calculators 74, 88 can be implemented in software in a personal computer having a data acquisition port for accepting outputs for the temperature sensors 70, 72, 78 and 80.

The output signals from the thermal flow calculators 74, 88 are communicated as flow signals to the subtractor 22 and divider 24 as described hereinbefore with respect to outputs from the main flow sensor 18 and the waste flow sensor 20.

In an alternative embodiment, (not shown) tubes carrying mobile phase flow from the pump 26 and to the flow-divider 12 are disposed adjacent to each other. A common heater is used to heat the flows through both paths. Temperature sensors are disposed downstream in each tube at substantially identical distances from the heater. Because a common heater is used, the tubing and temperature sensors are placed in close proximity and the difference between the thermal signals is calculated electronically, a high degree of common-mode noise rejection is achieved. Such effective noise rejection allows measurements of minute differences between the flow rate in the main flow path 10 and the flow rate in the waste flow path 16.

Although the embodiments of the invention that are depicted in FIGS. 4–7 use a variable restrictor 29 in the waste flow path 16, the flow in the operating flow path 14 could also be controlled by varying the flow controls of the pump 26.

Figure 8:
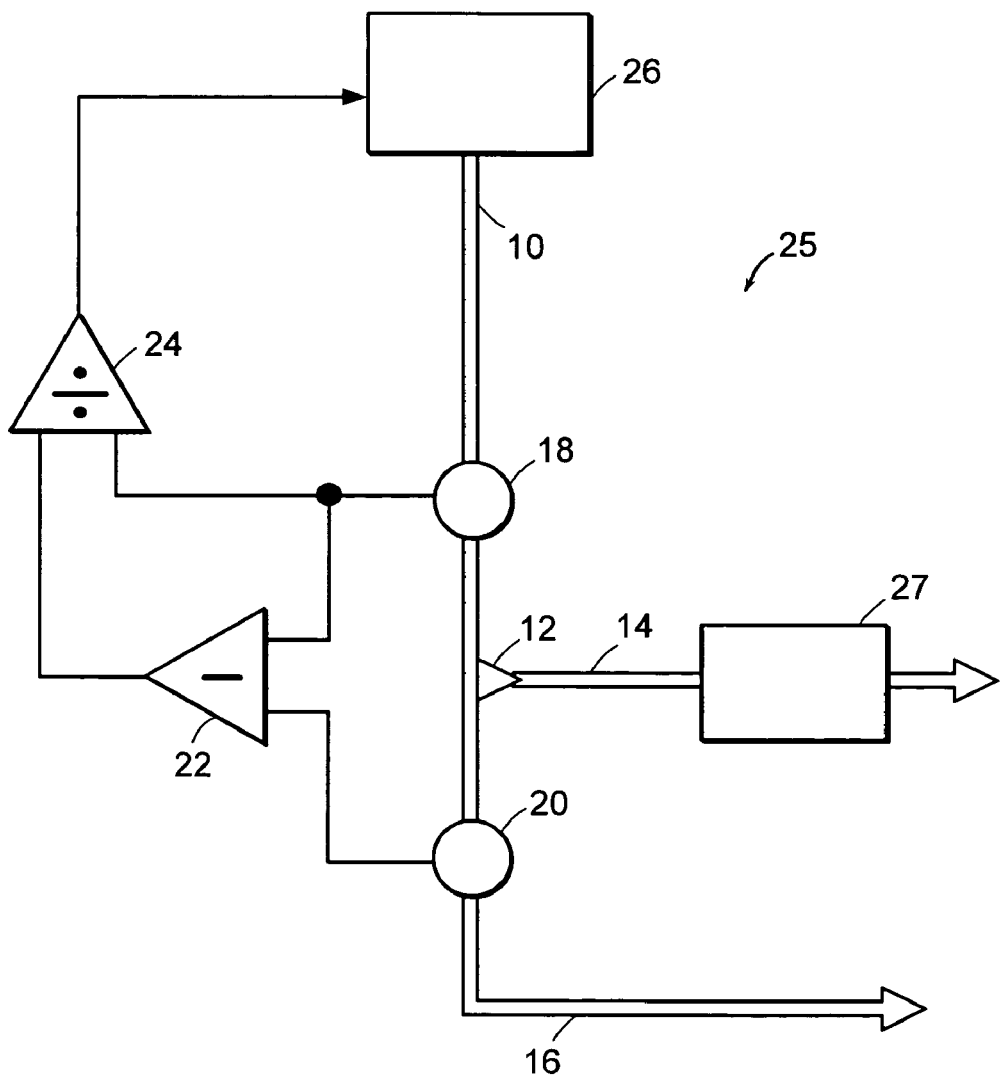
FIG. 8 is a schematic system diagram of an apparatus for measuring and controlling nano-scale flow rates in a capillary system using feedback signals to control the system pump according to an illustrative embodiment of the present invention.

In another embodiment of the invention, the flow rate in the operating stream can be controlled by directly adjusting the pump output to the main stream rather than by adjusting any variable restrictor. For example, FIG. 8 illustrates an embodiment of the invention wherein the flow rate in the operating stream is controlled by adjusting pump 26 settings in response to variations in the measured flow. In FIG. 8, (as in the embodiments described in FIG. 3) a main flow path 10 is divided by a flow-divider 12 into an operating flow path 14 and a waste flow path 16. A main flow sensor 18 is operatively disposed in the main flow path 10. A waste flow sensor 20 is operatively disposed in the waste flow path 16. Outputs from both the main flow sensor 18 and the waste flow sensor 20 are connected to the input of a subtractor 22 for communicating volumetric flow rate signals to the subtractor 22. Outputs from both the main flow sensor 18 and the subtractor 22 are connected to inputs of a divider 24 for communicating the main volumetric flow rate signal and a difference signal to the divider 24. The output from the divider 24 is operatively connected to the pump 26 for adjusting the pump settings.

Persons skilled in the art should appreciate that additional control circuitry (not shown) may be required between the output of the divider 24 and the control input of the pump 26. For example, additional control circuitry may be implemented to condition the divider output signal (quotient signal) for use as an appropriate control input to the particular pump 26 being used. Circuit component such as buffers, inverters, amplifiers and/or microcontrollers, for example, can be used to implement the control circuitry according to a number of methods that are well known in the art. Alternatively, the pump 26 may be controlled by a personal computer or workstation (not shown) having input/output circuitry connected to the pump 26 and divider 24 and having software which adjusts the pump setting in response to the quotient signal output from the divider 24.

Figure 2:
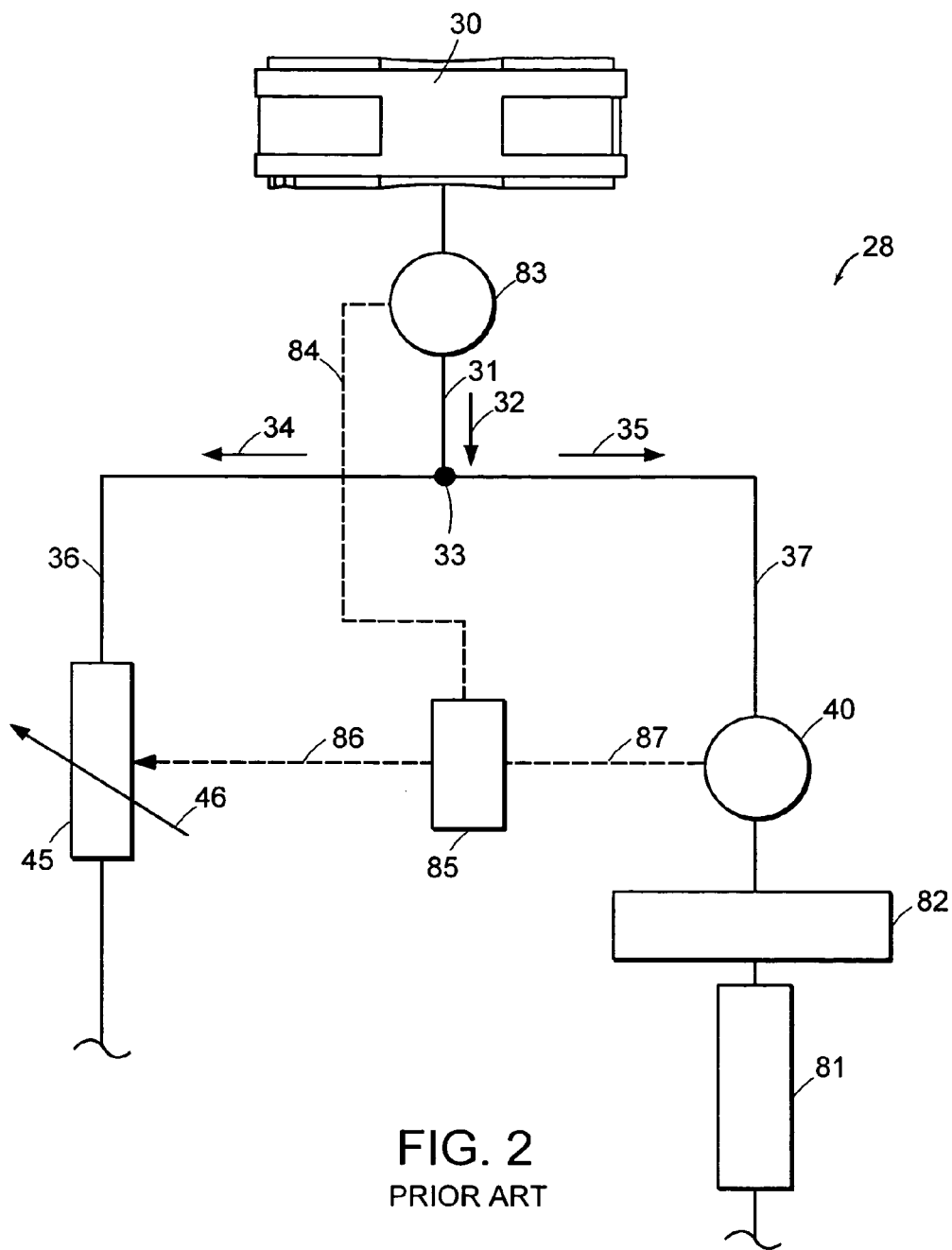
FIG. 2 is a schematic system diagram of an apparatus for measuring volumetric flow rates of liquids in capillaries according to the PRIOR ART.

Although embodiments of the present invention are described hereinbefore as having a first flow detector in the main flow path and a second flow detector in the waste flow path, an additional embodiment of the present invention is implemented by disposing the second flow detector in the operating flow path rather than the waste flow path. This additional embodiment provides advantages over the prior art described hereinbefore with respect to FIG. 2 because, unlike the prior art, the outputs from the two flow detectors are used to produce a quotient signal that represents the split ratio which is independent of the varying liquid composition.

Figure 9:
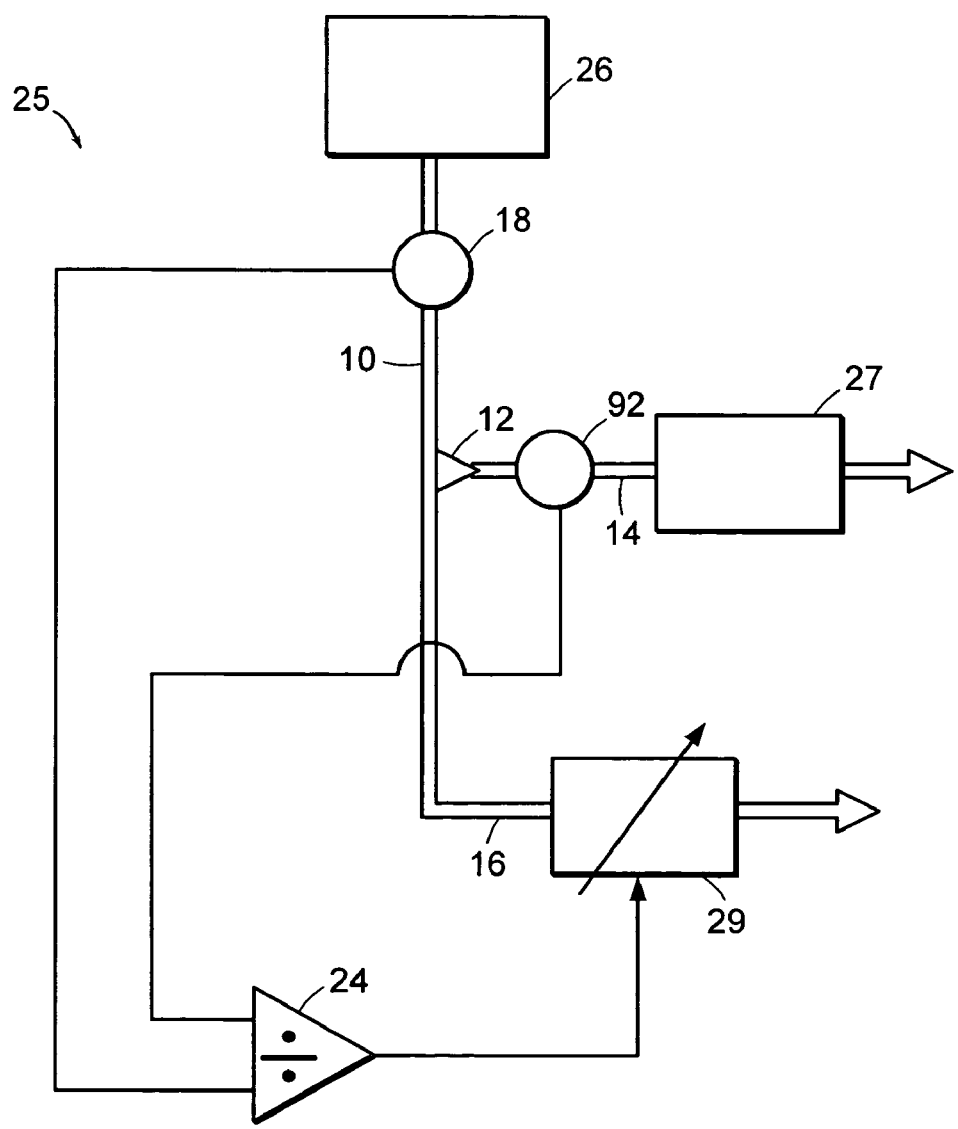
FIG. 9 is a schematic diagram of an apparatus for measuring and controlling nano-scale flow rates in a capillary system using feedback signals from a sensor in the operating flow path according to an alternative embodiment of the present invention.

The additional embodiment is described with reference to FIG. 9 in which a main flow path 10 is divided by a flow-divider 12 into an operating flow path 14 and a waste flow path 16. A main flow sensor 18 is operatively disposed in the main flow path 10. An operating flow sensor 92 is operatively disposed in the operating flow path 14. Outputs from both the main flow sensor 18 and the operating flow sensor 20 are connected to inputs of a divider 24 for communicating the main volumetric flow rate signal and operating stream flow rate signal to the divider 24. The output of the divider 24 can be used, for example as described hereinafter to control flow rate in an operating stream. The flow rate in the operating stream can be controlled, for example, by adjusting a the permeability of a waste path variable resistor, in the form of a variable restrictor 29 disposed in the waste flow path 16 and operatively connected to the output of the divider 24 and/or by adjusting the flow rate controls of the pump 26.

Figure 10:
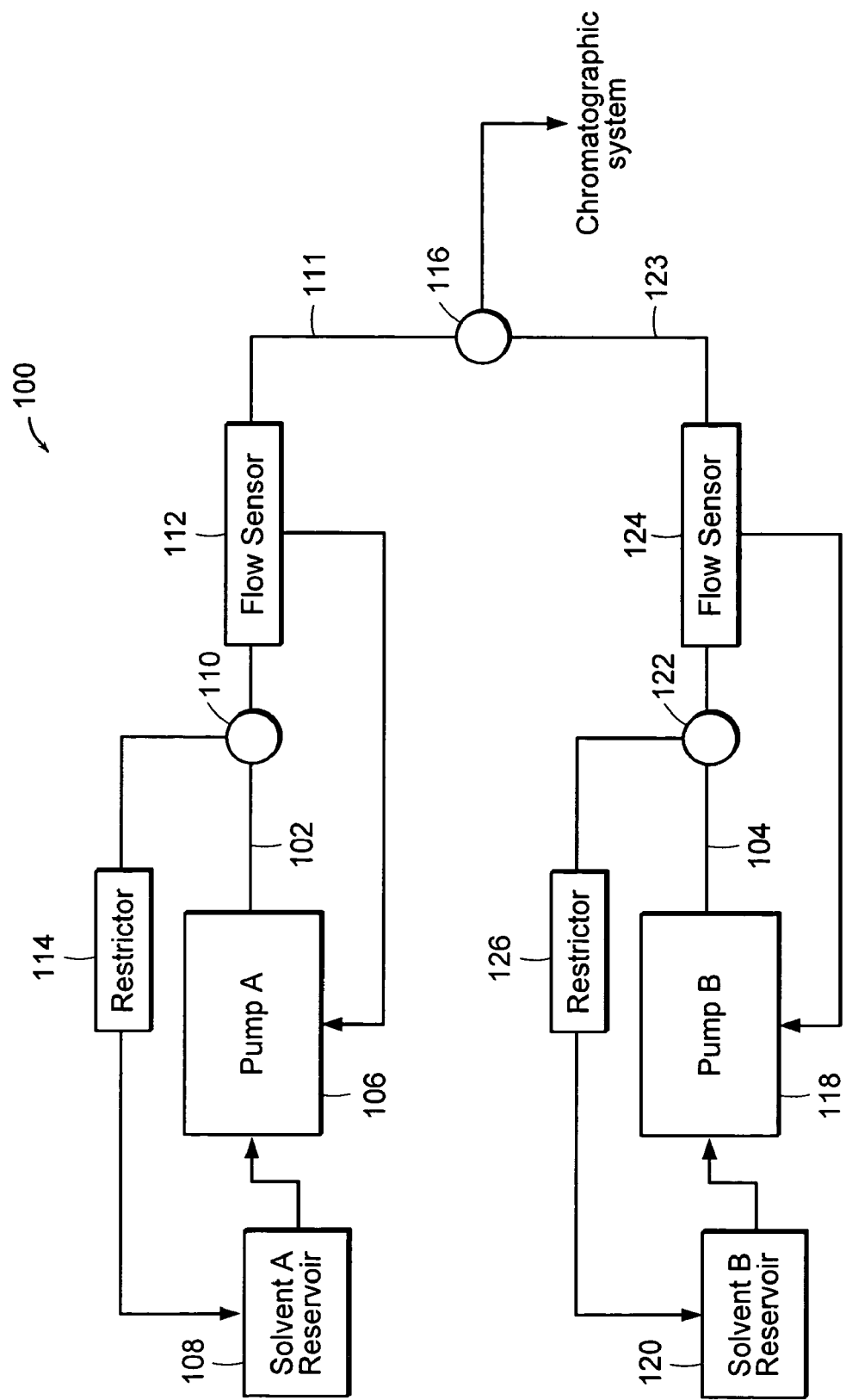
FIG. 10 is a schematic diagram of an apparatus for measuring and controlling nano-scale flow rates in a recycling closed-loop flow control binary solvent delivery system according to an alternative embodiment of the present invention.

An illustrative embodiment of a binary solvent delivery system 100 according to the present invention is described in reference to FIG. 10. The binary solvent delivery system 100 has a first operating path 102 and a second operating path 104 allowing the formation of a solvent gradient. The first operating path 102 has a first pump 106 having a first solvent reservoir 108. The first pump 106 is in fluid communication with a first flow splitter 110. The first flow splitter 110 is in fluid communication with a first sensor flow path 111 having a first flow sensor 112. The first flow splitter 110 is in further fluid communication with a first flow restrictor 114. The first flow restrictor 114 is in fluid communication with the first solvent reservoir 108. The first flow sensor 112 is in fluid communication with a fluidic tee 116. The first flow sensor 112 produces an output signal that is in communication with the control system of the first pump 106. The flow rate of the first pump 106 can be controlled by the output signal of the first flow sensor 112.

The second operating path 104 has a second pump 118 having a second solvent reservoir 120. The second pump 118 is in fluid communication with a second flow splitter 122. The second flow splitter 122 is in fluid communication with a second sensor flow path 123 having a second flow sensor 124. The second flow splitter 122 is in further fluid communication with a second flow restrictor 126. The second flow restrictor 126 is in fluid communication with the second solvent reservoir 120. The second flow sensor 124 is in fluid communication with the fluidic tee 116. The second flow sensor 124 produces an output signal that is in communication with the control system of the second pump 118. The flow rate of the second pump 118 can be controlled by the output signal of the second flow sensor 124.

In operation, a portion of the flow from each pump 106, 118 is diverted to its respective solvent reservoir 107, 120 via their respective flow splitters 110, 122. The diversion of flow into each respective solvent reservoir 107, 120 is in response to the permeability of the flow restrictors 114, 126. The permeability of each flow restrictor 114, 126 is selected to attain a desired recycle ratio. In operation, if a flow rate of about 1 µL/min is required and the optimal flow rate for a pump used is about 100 µL/min, a restrictor can be selected that will recycle about 99 percent of the pump output back to the solvent reservoir. By recycling such excess solvent flow from the respective pumps prior to mixing, flow that is not directed to the chromatographic system can be recycled back into the solvent reservoir thus eliminating solvent waste. It contemplated within the scope of the invention that such excess solvent can be sent to waste.

Figure 11:
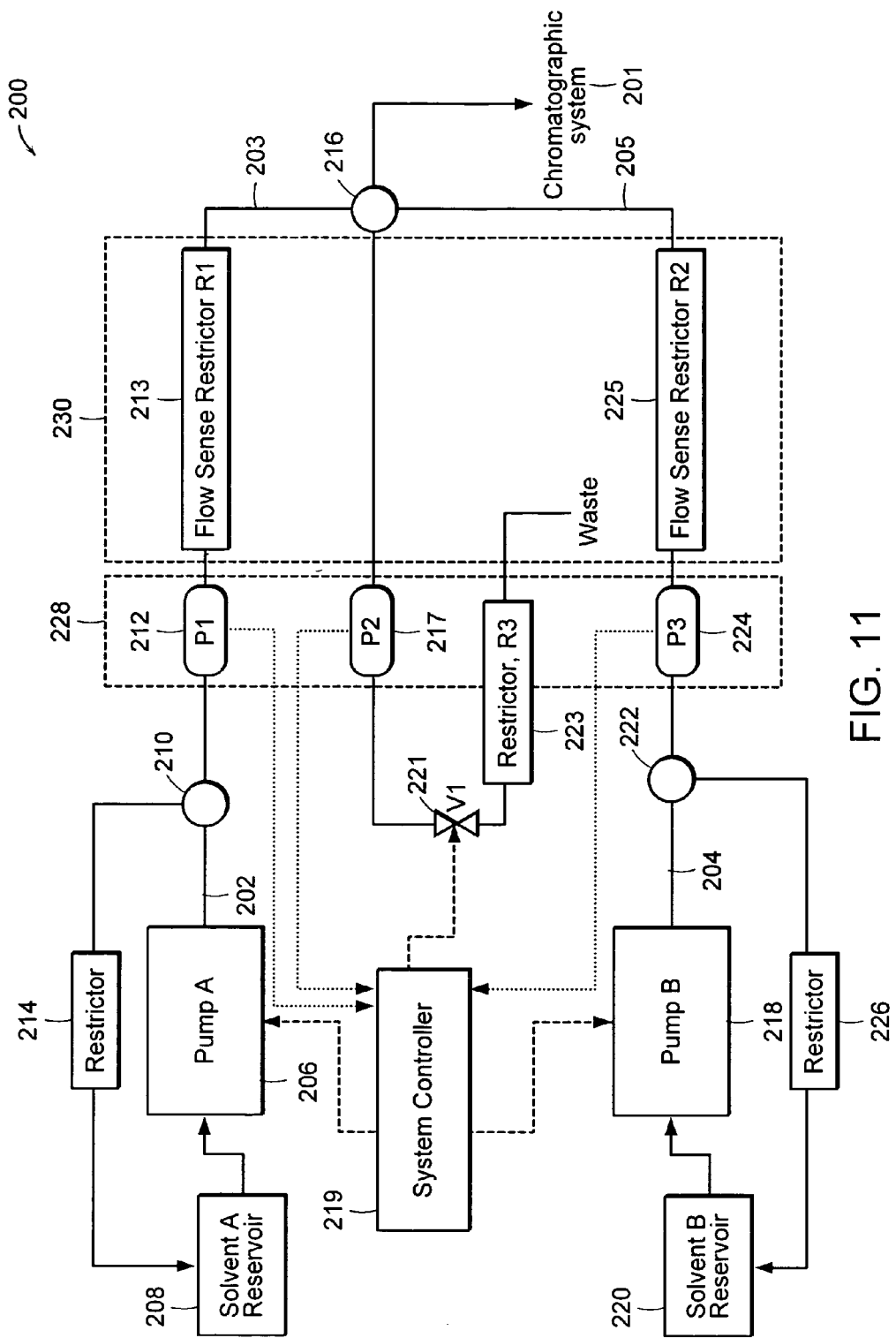
FIG. 11 is a schematic diagram of an apparatus for measuring and controlling nano-scale flow rates in a recycling closed-loop flow control binary solvent delivery system with delta-P flow sensors and sensor venting control according to an alternative embodiment of the present invention.

A further illustrative embodiment of a binary solvent delivery system 200 according to the present invention is described in reference to FIG. 11. The binary solvent delivery system 200 has a first flow path 202 and a second flow path 204 allowing the formation and delivery of a solvent gradient to a chromatographic system 201. The first flow path 202 has a first pump 206 having a first solvent reservoir 208. The first pump 206 is in fluid communication with a first flow splitter 210. The first flow splitter 210 is in fluid communication with a first pressure flow path 203 having a first pressure transducer 212 and a first flow restrictor 214. The first flow restrictor 214 is in fluid communication with the first solvent reservoir 208. It is contemplated within the scope of the invention that flow from the first flow restrictor 214 can be diverted to waste. The first pressure transducer 212 is in fluid communication with a first flow sense restrictor 213. The first flow sense restrictor 213 is in fluid communication with a fluidic tee cross 216. The fluidic tee cross 216 is in fluid communication with a fluidic cross pressure transducer 217. In this illustrative embodiment, the first pressure transducer 212, the fluidic cross pressure transducer 217 and the first flow sense restrictor 213 form a delta-P type flow sensor.

The second flow path 204 has a second pump 218 having a second solvent reservoir 220. The second pump 218 is in fluid communication with a second flow splitter 222. The second flow splitter 222 is in fluid communication with second pressure flow path 205 having a second pressure transducer 224 and a second flow restrictor 226. The second flow restrictor 226 is in fluid communication with the second solvent reservoir 220. It is contemplated within the scope of the invention that flow from the second flow restrictor 226 can be diverted to waste. The second pressure transducer 224 is in fluid communication with a second flow sense restrictor 225. The second flow sense restrictor 225 is in fluid communication with the fluidic tee cross 216. The second pressure transducer 224 produces an output signal that is in communication with the system controller 219. In this illustrative embodiment, the second pressure transducer 224, the fluidic cross pressure transducer 217 and the second flow sense restrictor 225 form a delta-P type flow sensor.

The first pressure transducer 212 and the second pressure transducer 224 produce an output signal that is in communication with a system controller 219. The fluidic cross pressure transducer 217 also produces an output signal that is in communication with the system controller 219. The fluidic cross pressure transducer 217 is in fluid communication with a control valve 221. The control valve 221 is in communication with the system controller 219. The control valve 221 in this first illustrative embodiment is in fluid communication with a waste restrictor 223.

In operation, a pressure drop measurement between the first pressure transducer 212 and the fluidic cross pressure transducer 217 and the second pressure transducer 224 and the fluidic cross pressure transducer 217 will be proportional to the flow delivered by the first pump 206 and the second pump 218 respectively. The system controller 219 has the capacity to determine the flow rates from the first pump 206 and second pump 218 using these pressure drop measurement differences in conjunction with previously derived flow calibration constants. In addition to measuring these flow rates, the system controller 219 employs a closed-loop control algorithm such as proportional integral control (PI) or proportional integral derivative control (PID) to adjust the first pump 206 and second pump 218 flow delivery rates to achieve the total flow and solvent composition delivered to a chromatographic system 201.

The pressure transducers 212, 224, in this illustrative embodiment are flow through transducers that in operation are flushed constantly by solvent. The fluidic cross pressure transducer 217 is also a flow through transducer that measures the pressure at the fluidic cross 216. By placing the fluidic cross pressure transducer 217 in this position it can be used by both pressure transducers 212, 224 to determine the respective flow rates in the pressure flow paths 203, 205. It is contemplated within the scope of the invention, however, that each pressure flow path 203, 205 can have two pressure transducers.

In order to accurately measure the fluidic cross 216 pressure by the fluidic cross pressure transducer 217, its flow exit must be capped so no flow can pass through it. This configuration can cause problems in several situations. During the system 200 startup or initialization, the system 200 may contain air in the fluidic tubing forming the respective flow paths 202, 204 and pressure flow paths 203, 205. Air trapped in the fluidic cross pressure transducer 217 or the lines leading to it will be trapped if the exit of the fluidic cross pressure transducer 217 is capped. This trapped air may create an unknown fluidic capacitance in the system. Also, during gradient operation of the system 200, because the tubing leading to fluidic cross pressure transducer 217 is not continuously flushed, fluid may flow into or out of this tubing into the flowing stream during system pressure changes.

Solvent mixtures from a prior gradient run may vent into a subsequent gradient run causing unknown solvent composition changes. To mitigate these effects, the waste valve 221, and/or the waste restrictor 223 at the exit of fluidic cross pressure transducer 217 is used to vent trapped air. During system 200 initialization, the waste valve 221 can remain open to allow solvent to be flushed through the fluidic cross pressure transducer 217, eliminating any trapped air. It is contemplated within the scope of the invention that the waste valve 221 could be opened momentarily during, or at the start or end of a gradient run by the system controller 219 to flush solvent trapped in the fluidic cross pressure transducer 217 or tubing leading to it.

In a further illustrative embodiment the waste restrictor 223, is selected to allow a nominal amount of solvent to continuously flow through fluidic pressure transducer 217 during operation of the system 200. The flow through the fluidic pressure transducer 217 using the waste restrictor 223 is a small percentage of the total flow to the chromatographic system (i.e. <1%). Advantageously, the low flow through the waste restrictor 223 allows a constant flushing flow of the fluidic cross pressure transducer 217 and the tubing connecting it to the fluidic cross 216. The waste restrictor 223 can be tuned or selected ensuring that this constant flushing flow does not effect the chromatography.

When using pressure transducers as delta-P type flow sensors, in order to obtain accurate flow measurements using differences in the three pressure transducers 212, 217, 224 it is desirable that the zero point of each pressure transducer 212, 217, 224 be maintained at a constant. A common source of zero point drift in strain-gage pressure transducers is transducer temperature fluctuations. Strain-gage pressure transducers measure changes in the resistance of strain elements to determine pressure. The strain element's resistance will also change with temperature. If one or more of the three pressure transducers 212, 217, 224 zero point changes due to temperature fluctuations, difference calculations used to measure flow rate will be inaccurate. For consistent and reproducible results the three pressure transducers 212, 217, 224 in a first illustrative embodiment, may be contained in a first isothermal block 228. In addition, the flow sense restrictors 213, 225 used in conjunction with the pressure transducers 212, 217, 224 may also be maintained in a second isothermal block 230. The temperature of the flow sense restriction elements 213, 225 must be maintained at approximately the temperature they were calibrated. Changes in the temperature of the flow sense restriction elements 213, 225 will result in erroneous flow measurements as temperature-induced viscosity changes of the fluid inside the flow sense restriction elements 213, 225 change the pressure difference across the flow sense restriction element 213, 225. While the pressure transducers 212, 217, 224 and the flow sense restriction elements 213, 225 can be maintained at isothermal temperature, it is not necessary that they are maintained at the same temperature.

In yet a further illustrative embodiment, the system controller 219 compensates for flow lost due to this constant flushing flow by estimating the flushing flow rate based upon the waste restrictor 223 parameters and the system pressure and adding this to the flow delivered by pumps through feedback to the pressure transducers 212, 224.

Although flow sensors are described herein in terms of specific thermal type flow sensors and pressure-type flow sensors, persons skilled in the art should appreciate that any number of various flow sensor types may be substituted therefor without departing from the spirit and scope of the present invention. For example several types of commercially available sensors can be used as main stream flow sensors and/or waste stream flow sensors according to the present invention.

Although various embodiments of the present invention are described herein in terms of separate circuit components for comparing pressure or temperature from various sensor components, persons skilled in the art should appreciate that a single circuit component can be implemented to serve multiple comparison functions according to the present invention. For example, a single microcontroller having multiple measurement input ports and control output ports can be used to receive and process upstream and downstream temperature and/or pressure signals to compute main path waste path flow rates and generate output signals for communicating to the subtractor and divider. An application specific integrated circuit (ASIC) could also be designed, for example, to perform these functions as well as incorporating the functions of the subtractor and divider, either by digital or analog operation, without departing from the spirit and scope of the present invention.

Although embodiments of the present invention are described herein which control flow rates in the operating stream indirectly by controlling a variable restrictor in the waste flow path or the main flow path, or by controlling the pump or variable split vent, persons skilled in the art should appreciate that these various control elements could be also implemented in various combinations according to the present invention.

Although the various embodiments of the present invention are described for use in measuring nano-scale flow rates in an HPLC system, persons skilled in the art should appreciate that the present invention can be used to measure and control a variety of different capillary systems, or fluid control and analysis systems without departing from the spirit and scope of the invention.

Although the invention is described hereinbefore with respect to illustrative embodiments thereof, persons having ordinary skill in the art should appreciate that the foregoing and various other changes, omissions and additions in the form and detail thereof may be made without departing from the spirit and scope of the invention.

What is claimed is:

1. An apparatus for forming a gradient composition in a chromatographic capillary system comprising:

a first flow path having a first pump in fluid communication with a first flow divider said first flow divider being in fluid communication with a first restrictor operatively disposed in a first restrictor flow path and a first sensor flow path with a first sensor operatively disposed within said sensor flow path said first sensor configured to measure flow rates of said liquid in said first sensor flow path to produce a first flow signal said first restrictor having a selected permeability producing a first flow rate;

a second flow path having a second pump in fluid communication with a second flow divider said first flow divider being in fluid communication with second restrictor operatively disposed in a second restrictor flow path a second sensor flow path with a second sensor operatively disposed in said second sensor flow path said second sensor configured to measure flow rates of said liquid in said second sensor flow path to produce a second flow signal said second restrictor having a selected permeability producing a second flow rate;

means for combining the first sensor flow path and the second flow path; and means for controlling flow in first and second sensor flow paths to form a gradient composition.

2. The apparatus according to claim 1, wherein said capillary system comprises a high pressure liquid chromatography (HPLC) system having flow rates in a range of approximately 50 nL/min to approximately 100 µL/min.

3. The apparatus according to claim 1, wherein said sensors are thermal-type flow sensors.

4. The apparatus according to claim 3, wherein said thermal-type flow sensor comprises:

means for introducing heat in a flow path;

means for measuring temperature of liquid in said flow path upstream and downstream of said means for introducing; and means for computing volumetric flow rate of liquid in said flow path according to temperature changes measured upstream of said means for introducing compared to temperature changes measured downstream of said means for introducing in response to introduction of said heat.

5. The apparatus according to claim 1, wherein said sensors are pressure-type flow sensors.

6. The apparatus according to claim 5, wherein said pressure-type flow sensors comprise:

restrictor means disposed in a flow path;

means for measuring fluid pressure upstream and downstream of said restrictor means; and means for computing volumetric flow rate of liquid in said flow path according to a difference between pressure measured upstream of said restrictor means and pressure measured downstream of said restrictor means.

7. The system according to claim 1, wherein said means for controlling comprises a controller receiving said first flow signal and said second flow signal from said sensors and configured to adjust liquid flow rate in said sensor flow paths in response to said flow signals.

8. The system according to claim 7, wherein said first flow restrictor and said second flow restrictor are responsive to a signal from said controller configured to adjust said liquid flow rate in said first and second sensor flow paths by varying permeability of said restrictor flow paths.

9. The system according to claim 1, wherein first and second pumps are responsive to signals from said controller to adjust said liquid flow rates in said first and second sensor flow paths by varying output pressure of said first and second pumps.

10. An apparatus for measuring flow rates of a liquid in a chromatographic capillary system comprising:

a first flow-divider and a second flow-divider;

a first flow path carrying liquid to said first flow-divider;

a second flow path carrying liquid to said second flow-divider;

a first pressure flow path carrying a first portion of said liquid from said first flow-divider;

a second pressure flow path carrying a first portion of said liquid from said second flow-divider;

a first recycle flow path carrying a second portion of said liquid from said first flow-divider;

a second recycle flow path carrying a second portion of said liquid from said second flow divider;

a first pressure transducer operatively disposed in said first pressure flow path and configured to measure pressure of said liquid in said first pressure flow path to produce a first pressure flow path signal said first pressure transducer being in fluid communication with a first flow sense restrictor a second pressure transducer operatively disposed in said second pressure flow path and configured to measure pressure of said liquid in said second pressure flow path to produce a second pressure flow signal said second pressure transducer being in fluid communication with a second flow sense restrictor;

a fluidic cross in fluid communication with said first and second flow sense restrictors;

a fluidic cross pressure transducer in fluid communication with said fluidic cross and configured to measure pressure at said fluidic cross to produce a fluidic cross pressure signal; and a controller receiving said first pressure flow signal and said second pressure flow signal and said fluidic cross pressure signal and providing an output representing said first pressure flow rate and said second pressure flow rate.

11. The apparatus according to claim 10 further comprising a control valve in fluid communication with said fluidic cross pressure transducer said control valve in further fluid communication with a waste restrictor said control valve in communication with said controller.

12. The apparatus according to claim 11 wherein said waste restrictor allows a continuous flow through said fluidic cross pressure transducer.

13. The apparatus according to claim 10 wherein said pressure transducers and said flow sense restrictors are further contained within a isothermal block.

14. The apparatus according to claim 10 wherein said capillary system comprises a high pressure liquid chromatography (HPLC) system having pressure path flow rates in a range of approximately 1 nL/min to approximately 100 µL/min.

* * * * *